United States Patent [19]

Cohen

[11] Patent Number: 4,691,709

[45] Date of Patent: Sep. 8, 1987

[54] APPARATUS FOR MEASURING VELOCITY OF BLOOD FLOW IN A BLOOD VESSEL

[75] Inventor: Donald M. Cohen, Encino, Calif.

[73] Assignee: Cordis Corporation, Dade, Fla.

[21] Appl. No.: 911,375

[22] Filed: Sep. 25, 1986

Related U.S. Application Data

[63] Continuation-in-part of Ser. No. 881,476, Jul. 1, 1986, which is a continuation of Ser. No. 671,913, Nov. 16, 1984, abandoned.

[51] Int. Cl.$^4$ .............................................. A61B 5/02
[52] U.S. Cl. .................................. 128/667; 128/692; 128/748; 128/675; 73/705
[58] Field of Search ...................... 128/634, 665–667, 128/748, 691, 692, 675; 73/705

[56] References Cited

U.S. PATENT DOCUMENTS

| | | | |
|---|---|---|---|
| 3,273,447 | 9/1966 | Frank | 128/675 X |
| 3,822,695 | 7/1974 | Takayama | 128/634 |
| 4,201,222 | 5/1980 | Haase | 128/667 |
| 4,210,029 | 7/1980 | Porter | 128/634 |
| 4,487,206 | 12/1984 | Aagand | 128/634 |

FOREIGN PATENT DOCUMENTS 3855  9/1985  PCT Int.'l Appl. ................ 128/667

OTHER PUBLICATIONS

Murgo et al., Proc. IEEE, vol. 65, No. 5, May 1977, pp. 696–702.

Angelakos, Amer. J. Med. Elec., Oct.–Dec. 1964 pp. 266–270.

Pieper, Rev. Sci. Instr., vol. 29, No. 11, Nov. 1958, pp. 965–967.

Primary Examiner—Kyle L. Howell
Assistant Examiner—John C. Hanley
Attorney, Agent, or Firm—Tarolli, Sundheim & Covell

[57] ABSTRACT

Apparatus is provided for measuring the velocity of blood in a blood vessel in a body as well as for measuring static pressure at one or more sites within the blood vessel. The apparatus employs an elongated optical fiber member carried within a tubular catheter having a proximal end and a distal end with the latter adapted to be inserted within a blood vessel so that the blood flowing therein is parallel to the catheter. A first pressure transducer is carried by the catheter adjacent the distal end thereof and responds to static pressure acting transversely of the catheter for modulating the intensity of any light passing through the optical fiber inversely proportional to the magnitude of the transversely acting static pressure. A second pressure transducer is carried by the catheter at the distal end thereof and responds to total pressure including both static and kinetic pressure, acting parallel to the catheter, and which modulates the intensity of any light passing through the optical fiber proportional to the magnitude of the total pressure. This permits the velocity of blood flowing in the blood vessel to be determined as a function of the difference between the total pressure and the transversely acting static pressure.

14 Claims, 28 Drawing Figures

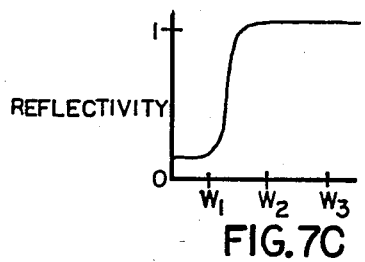
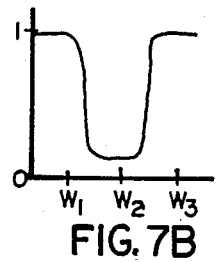
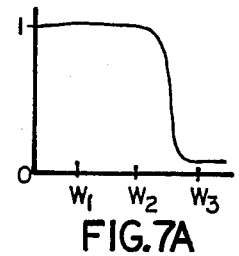
FIG. 7C    FIG. 7B    FIG. 7A
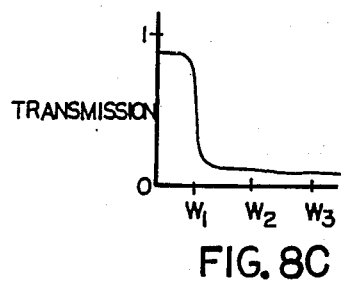
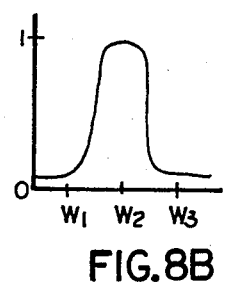
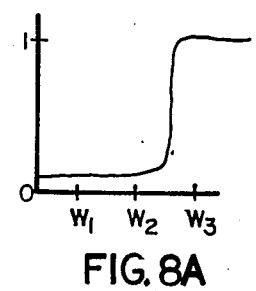
FIG. 8C    FIG. 8B    FIG. 8A
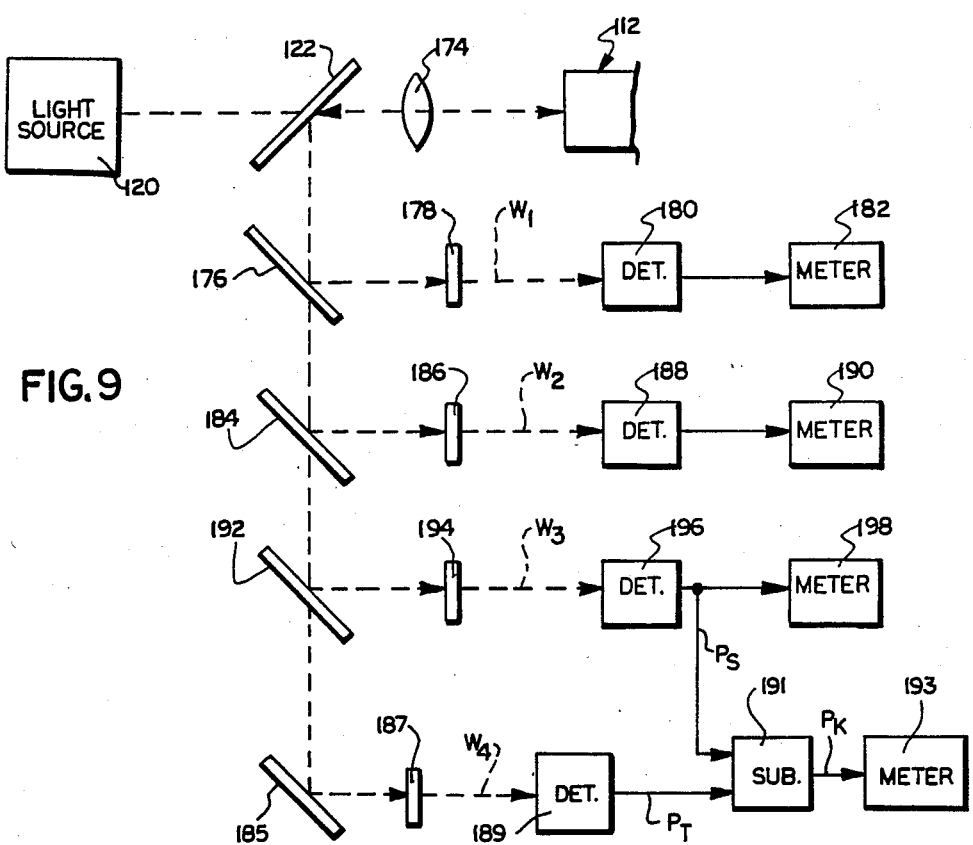
FIG. 9

APPARATUS FOR MEASURING VELOCITY OF BLOOD FLOW IN A BLOOD VESSEL

RELATED APPLICATION

This is a continuation-in-part of my previously filed U.S. application Ser. No. 881,476, filed July 1, 1986, which is a continuation of Ser. No. 671,913, filed Nov. 16, 1984 now abandoned, entitled "Improved Optical Fiber Pressure Transducer" and assigned to the same assignee as the present invention.

BACKGROUND OF THE INVENTION

This invention relates to the art of measuring parameters of blood within the cardiovascular system and, more particularly, to apparatus for directly measuring the velocity of blood flowing at a location of interest within a blood vessel by means of a catheter having a transducer tip insertable into the blood vessel.

It is known in the art to employ optically based catheters for use in measuring blood pressure within a cardiovascular system. Such devices typically employ a pressure transducer located at the distal end of a catheter which is insertable within a blood vessel for measuring blood pressure at a site of interest. Such devices typically take the form as illustrated in U.S. Patents to Polyanyi, U.S. Pat. No. 3,249,105 and Franke, U.S. Pat. No. 3,215,135. Each of these devices employs a catheter having fiber optic means extending the length of the catheter to the distal end thereof at which the fiber optic means is in optical communication with a pressure transducer. The pressure transducers in Polyanyi and Franke, supra, take the form of a diaphragm covering the end hole of a catheter. The diaphragm is located in front of or distal to the end of the optical fiber means and receives light and reflects it back into the fiber optic means for transmission to an externally located meter. Since the transducer is inserted into the bloodstream of a patient, the blood pressure deflects the diaphragm causing modulation of the light intensity so that the meter provides an indication of blood pressure.

During blood flow conditions, such catheters employing diaphragm covered end holes measure total pressure including both kinetic pressure and static pressure. That is, by aligning the end hole of a catheter with the direction of blood flow, kinetic energy terms are introduced. If the catheter end hole is directed upstream, a kinetic term will be added to the pressure, and, if the end hole is facing downstream, the kinetic term will be subtracted from the pressure. The magnitude of the error will vary with the velocity and density of the fluid. This error will vary during the course of a cardiac cycle and will distort the shape and magnitude of a pressure wave. In the pulmonary artery, the kinetic pressure may be on the order of 10% of total pressure at rest and 50% of total pressure at a cardiac output equal to three times that at rest. The importance of the kinetic pressure error is particularly great in stenotic areas where velocities are high.

Catheters are known, however, which may be employed for measuring static pressure rather than total pressure, as in the case of the catheters discussed above. Such static pressure measuring catheters may employ side port monitoring of pressure rather than end hole monitoring of pressure. Thus, when pressure is measured perpendicular to blood flow, the kinetic contribution is minimal. One catheter for measuring static pressure has been described in a 1978 article entitled "The Development of Fibre Optic Catheter Tip Pressure Transducer", Journal of Medical Engineering and Technology, Volume 2, No. 5, by H. Matsumoto and M. Saegusa. As described there, a side port membrane is responsive to pressure perpendicular to blood flow and causes movement of a mirror, which is mounted in cantilevered fashion to the membrane, within a cavity of the transducer. The mirror serves to reflect light received from fiber optic means extending the length of the catheter so that the intensity of light returned by way of the fiber optic means to a measuring device located outside the body is modulated in accordance with the static pressure. Another catheter employing side port monitoring of pressure is disclosed in my aforesaid U.S. application Ser. No. 671,913 filed Nov. 16, 1984 entitled "Improved Optical Fiber Pressure Transducer." The catheter disclosed there employs an optical fiber having its cladding removed for a portion of its length and replaced with a transducer constructed of flexible light absorbing material which circumscribes the unclad portion of the optical fiber. When inserted into a blood vessel, only pressure which is exerted perpendicular to the optical fiber causes the light absorbing material to be compressed against the core of the optical fiber causing an increase in the absoption of the light transmitted through the fiber core. This provides a measure of static blood pressure.

The present invention improves upon that disclosed in my aforesaid application by combining such static blood pressure monitoring with total blood pressure monitoring in such a manner that the static pressure components may be factored out leaving only a kinetic blood pressure component in the presence of blood flow. Such a kinetic blood pressure component, then, serves as a measure of blood velocity at the site of interest within a blood vessel. Such blood velocity measurements are useful as an estimate of cardiac output. Cardiac output values assist in the determination of the effectiveness of a ventricular contraction. Additionally, such blood velocity measurements may be employed to indicate stenotic regions in the blood vessels. Such stenotic regions may be attributable to arthromatous disease. Currently, these stenotic regions are typically visualized by injecting a radiopaque dye and visualizing the flow of the dye through the blood vessel. The degree of narrowing or stenosis is expressed as a percentage of the non-stenotic region. The measurement of pressure gradients through the stenotic region is another method. However, neither method is a sensitive indicator of either arthromatous disease progression or vessel functionality. Moreover, in a stenotic area of a blood vessel, such as in a mildly stenotic region, there is little change in pressure or area, but there is a discernable change in blood velocity. Consequently, by monitoring blood velocity at a site of interest, information can be obtained providing an early indication of stenosis and can be used to assess the success of a recanalization procedure.

In addition to measuring blood velocity at a site of interest, the present invention also contemplates simultaneously measuring static blood pressure at one or more sites of interest. It is known, however, in the prior art to provide a multiple site pressure transducer for providing simultaneous measurement of static blood pressure at a plurality of sites. One such example is disclosed in the U.S. patent to D. C. Brown, U.S. Pat. No. 4,543,961 assigned to the same assignee as the present invention. However, Brown proposes measurements of but a single blood parameter; namely, static blood pressure. There is no teaching of measuring other blood parameters, such as blood velocity.

SUMMARY OF THE INVENTION

It is a primary object of the present invention to provide an improved catheter for use in measuring blood velocity in a blood vessel.

It is a still further object of the present invention to provide such a catheter for providing a measurement of blood velocity as a function of total pressure and static pressure.

It is a still further object of the present invention to provide such a catheter for measuring blood velocity while simultaneously measuring static blood pressure at one or more sites of interest.

In accordance with the present inventon, the foregoing and other objectives are achieved in a fiber optic based catheter system for measuring blood velocity in a blood vessel. The apparatus includes an elongated tubular catheter having a proximal end and a distal end with the latter adapted to be inserted into a blood vessel such that the blood flows parallel to the catheter. A first pressure transducer is carried by the catheter adjacent tne distal end thereof and responds to static pressure acting transversely of the catheter for modulating the intensity of any light passing through the optical fiber inversely proportional to the magnitude of the transversely acting static pressure. A second pressure transducer is carried by the catheter at the distal end thereof and responds to total pressure including both static pressure and kinetic pressure, acting parallel to the catheter, and which modulates the intensity of any light passing through the optical fiber proportional to the magnitude of the total pressure. This permits the velocity of blood flowing in the blood vessel to be determined as a function of the difference between the total pressure and the static pressure.

In accordance with another aspect of the present invention, both velocity and static pressure are measured.

In accordance with a still further aspect of the present invention, the catheter carries a plurality of static pressure transducers so that static pressure may be measured at a plurality of sites simultaneously with measuring blood velocity.

BRIEF DESCRIPTION OF THE DRAWINGS

The foregoing and other objects and advantages of the invention will become more apparent from a consideration of the following description as taken in conjunction with the accompanying drawings, wherein:

FIGS. 7A, 7B and 7C are graphical waveforms illustrating reflectivity versus wavelength useful in the description of the embodiment illustrated in FIGS. 5 and 6;

FIGS. 8A-8C are graphical waveforms illustrating light transmission as a function of wavelength and which is useful in the description of the embodiment of FIGS. 5 and 6;

FIG. 9 is a schematic-block diagram illustration of the optical system as well as the electronic detecting circuitry employed with the embodiment of FIGS. 5 and 6;

DETAILED DESCRIPTION OF PREFERRED EMBODIMENTS

Figure 1:
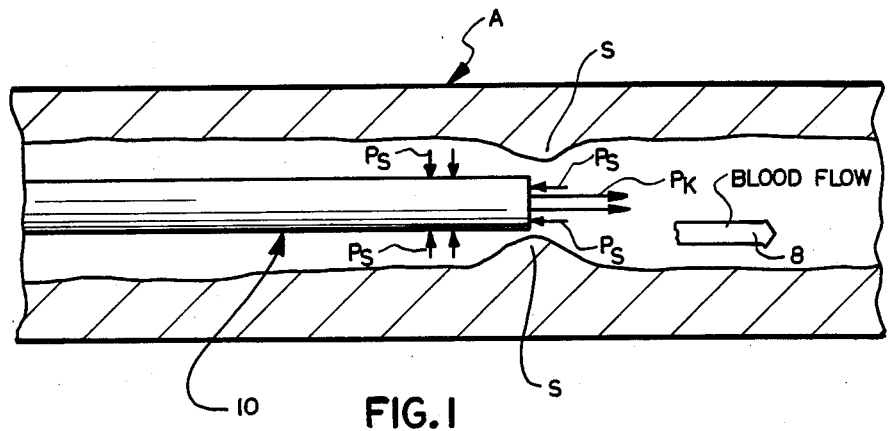
FIG. 1 is a schematic illustration showing one application of the present invention in conjunction with measuring the velocity of blood flowing within a patient's blood vessel.

Reference is now made to the drawings wherein the showings are for purposes of illustrating preferred embodiments only and not for limiting the same. FIG. 1 illustrates an application of the invention as applied to measuring blood velocity within a patient's blood vessel A by means of a catheter 10 constructed in accordance with the present invention. In this application, the patient's blood vessel A exhibits a low level of stenosis S, as is shown in the drawings. For such a mild stenosis, there may be very little change in pressure or area. However, there can be a discernable change in velocity in the area of the stenosis under test. Consequently, then, by measuring the velocity at the site of stenosis S, a measure can be had as to the degree of stenosis that has taken place. Also, the measurement of blood velocity in a blood vessel can also be used to provide an assessment of the success of a recanalization procedure wherein placque in a blood vessel has been removed, as with a laser beam. The catheter 10, which will be described in greater detail hereinafter, is provided with a side port pressure responsive transducer for measuring pressure acting transversely of the catheter and, hence, of blood flow indicated by the arrow 8. The catheter is also provided with an end hole transducer which responds to pressure acting parallel to that of the blood flow. In the absence of blood flow, only static pressure $P_S$ acts on the two transducers.

In accordance with the invention, the two transducers are optimized such that, in the absence of blood flow, the effects of static pressure acting transversely of and parallel to the catheter 10 are essentially cancelled out. The end hole transducer is responsive to total pressure which includes both static pressure $P_S$ as well as kinetic pressure $P_K$ (during the presence of a blood flow). However, since the static pressure components cancel out, only the kinetic pressure $P_K$ will be measured. Since velocity is a function of kinetic pressure, the measured kinetic pressure will provide an indication of blood velocity in the area of the stenosis S. More specifically, velocity is proportional to the square root of the measured kinetic pressure.

Figure 2:
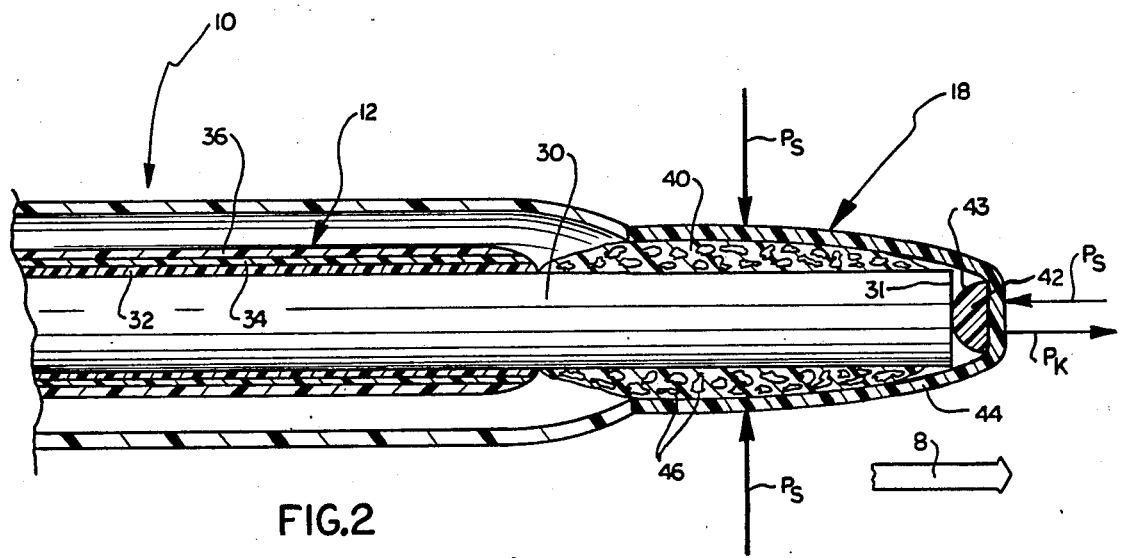
FIG. 2 is an enlarged sectional view of the distal end of the catheter employed in FIG. 1.

Having described an application of the invention as presented in FIG. 1, attention is now directed to a more detailed description of the transducer 18 in connection with FIG. 2. In FIG. 2, the transducer 18 is enlarged in size for ease in understanding the construction. The catheter 10 is a single lumen, thin walled catheter such as that provided by Cordis Corporation, and known as a Cordis FR5 thin wall catheter. This catheter may have a diameter on the order of 0.066 inches and is constructed of plastic material such as polyurethane. The catheter carries the optical fiber 12, taking the form in the preferred embodiment of FIG. 2 of a cladded single optical fiber. This fiber has a core 30 of acrylic material of a maximum diameter on the order of 368 micra. The core 30 is covered throughout essentially all of its length with cladding 32 constructed of a fluoropolymer having a thickness on the order of 16 micra. Surrounding the cladding 28 are Kevlar strands 34 for purposes of strengthening the optical fiber 30. The Kevlar strands 34 are, in turn, covered with a layer of black polyvinylchloride (PVC) 36.

The cladding 32, strands 34 and coating 36 are removed from the distal end and replaced with a sponge-like annular transducer ring 40. A protective membrane 44 extends from the distal end of the catheter and covers the annular transducer ring 40 and a reflective mirror 42, as seen in FIG. 2.

The removal of the cladding 32 may be accomplished in a controlled manner as with the use of a solvent, such as tetrahydrofluran, so that the removal takes place only at the tip of the optical fiber. The annular transducer ring 40 that encircles the uncladded end of the fiber is a sponge-like material, such as polyurethane foam. This may take the form of hypol foamable hydrophilic polyurethane polymer which may be obtained from the organic chemicals division of the W. R. Grace & Company. This is a porous material and includes interconnecting pores 46. The transducer ring 40 encircles the distal tip end of the uncladded core and is held in place as by an interference fit. The membrane 44 is of latex material and may be formed by dipping the distal end of the catheter, with the transducer ring 40 in place, into a viscous liquid of latex and then air drying it. The membrane, while covering the distal end of the cathether, will adhere and form a seal with the catheter, but does not adhere to the sponge-like material forming the transducer ring 40. The interior walls of the lumen at the distal end of the catheter may be coated with optically black material.

Figure 3:
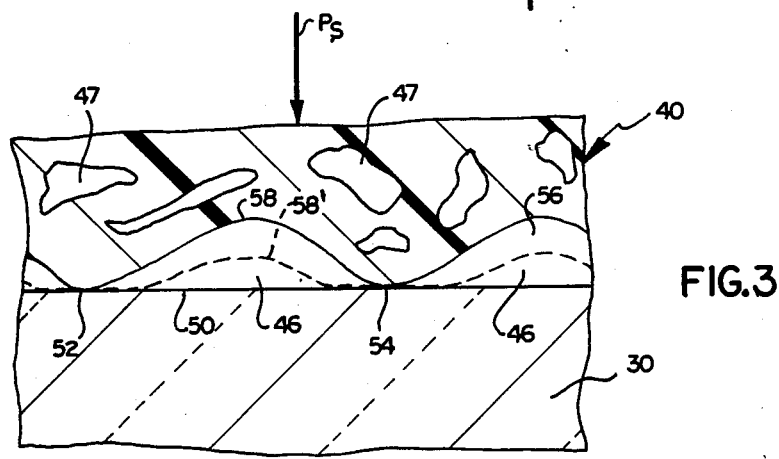
FIG. 3 is an enlarged view showing a portion of a transducer member in surface engagement with an uncladded core and used for purposes of explanation herein.

Reference is now made to FIG. 3 which is an enlarged showing of a portion of the length of the uncladded optical fiber core 30 in engagement with a portion of the transducer ring 40. The transducer material is sponge-like and has interconnected pores 46. Consequently, transducer ring 40 makes interrupted surface area contacts with the relatively smooth, uncladded surface 50 of the fiber core 30. As seen in FIG. 3, the transducer ring 40 makes surface engagement with the core surface 50 at various locations, such as 52 and 54, separated by an air pocket 56. The air pockets 56 are vented to the atmosphere by way of pores 46 and the annular space surrounding the cladded core within the lumen of the catheter 10 which leads to an aperture located at the proximal end of the catheter. This, then, provides the basis for a pressure differential with externally applied pressure. As the pressure increases, the interior surface 58 of ring 40 will move toward the uncladded surface 50, as indicated by the dotted lines 58', so as to increase the surface area contact with the uncladded surface 50. Likewise, as the pressure is removed, the sponge-like material, being resilient, will return to that as indicated by the solid line 58 in FIG. 3 and make less surface area contact with the uncladded surface 50. These variations in surface area contact between the transducer 40 and the uncladded surface of the optical fiber core 30 with variations in pressure modulate the intensity of light travelling through the optical fiber.

At this point, it is to be noted that the index of refraction n is different for the various materials employed. Thus, the index of the refraction n for the fiber core 30 is on the order of 1.5, and that for the surrounding air within the air pockets 46 and in the lumen, as vented to the atmosphere, is on the order of 1.0. The cladding 32 exhibits an index of refraction n of 1.4 which is slightly less than that of the core 30. Also, the index of refraction of the sponge-like material forming the transducer ring 40 is greater than that of the cladding 32 and optionally of the fiber core 30.

Light that travels through the core 30 and which strikes the core-air interface will be totally internally reflected. However, light that strikes the core-sponge interface will be partially refracted and partially reflected. The amount of light that is refracted, and, hence, absorbed will be a function of the surface contact area. Thus, light that is travelling from the proximal end to the distal end of the catheter will pass through the transducer area and a portion of the light will be absorbed in dependence upon the pressure. The light that is internally reflected will be reflected back by a reflective surface 43 on a flexible mirror 42. This reflected back light will also be attenuated as it passes the transducer area as it travels back toward the proximal end of the catheter. Consequently, then, the intensity of light returning at the proximal end of the catheter at the fiber leg 16 will vary inversely with the pressure forces P applied to the transducer.

The distal end of core 30 is preferably provided with a flat end surface 31 which is in abutting engagement with the convex surface of the flexible mirror 42. The flexible mirror 42 may be constructed of aluminized mylar, but in any event the concave surface 43 which abuts surface 31 is a reflective surface and may be held in place against surface 31 as with a transparent adhesive Light passing through the core 30 from its proximal end to its distal end will be reflected by the convex surface 43 of the flexible mirror 42 back toward the proximal end of the core. The amount of light reflected will vary with pressure applied to the mirror acting parallel to the direction of blood flow, as indicated by the arrow 8. In the absence of blood flow, only static pressure $P_S$ acts on the flexible mirror causing it to increase its area surface contact within surface 31 thereby increasing the amount of light returned to the proximal end. On the other hand, the static pressure exerted on the transducer ring 40 causes it to absorb more of the light transmitted through core 30. Preferably, the transducer ring 40 and the flexible mirror 42 are optimized such that as one absorbs more light, the other reflects more light in a like amount and, hence, cancel each other out or at the least provide a known offset. Consequently, during blood flow, the only variation in pressure which will affect the amount of light returning to the proximal end will be that resulting from the kinetic pressure $P_K$. As is seen from FIG. 2, the kinetic pressure will be in the direction of blood flow to either increase or decrease the amount of surface area contact between the concave surface 43 and the flat surface 31 at the distal end of core 30. This pressure variation will be indicated by the amount of light returning to the proximal end of the core 30 and present a measure of kinetic pressure $P_K$ and, hence, of blood velocity.

Having now presented a description of the invention as directed to the embodiment shown in FIGS. 1, 2 and 3, attention is now directed to the embodiments to be described hereinafter which present various embodiments wherein blood velocity is measured while simultaneously measuring static pressure at a plurality of sites.

Figure 4:
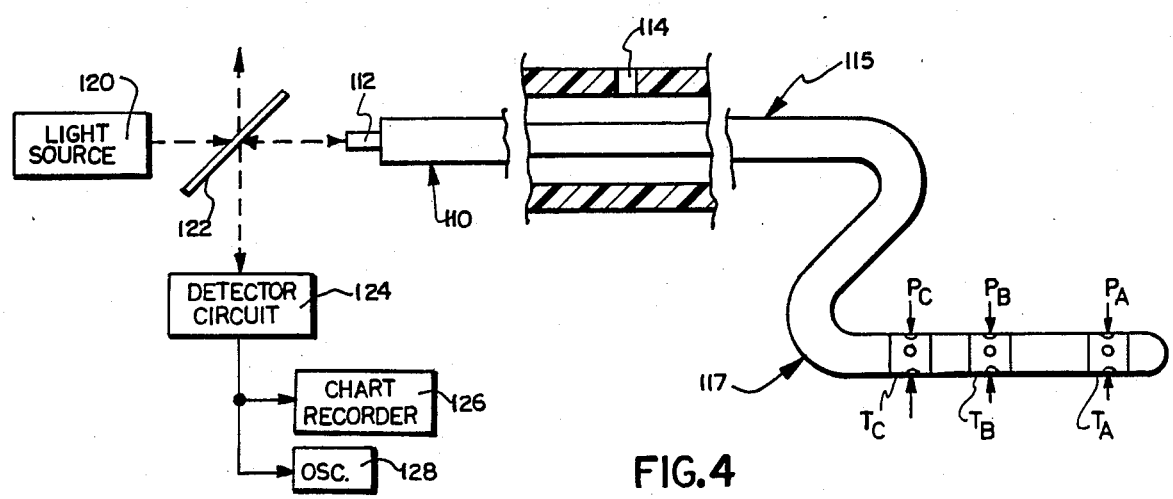
FIG. 4 is a schematic illustration of a multi-site pressure measuring catheter in conjunction with one application of the invention.

FIG. 4 illustrates an application of the invention as applied to simultaneous measurement of blood pressure as well as the velocity of blood within a patient's blood vessel. This includes an elongated single lumen catheter 110 containing an optical fiber 112 which extends throughout the length of the catheter. At its distal end, the catheter carries a filter F employed for use in measuring the velocity of blood. In addition, the catheter carries three blood pressure transducers $T_A$, $T_B$, and $T_C$ for simultaneously measuring the blood pressure within the cardiovascular system at three different sites, such as sites A, B and C. The spacing between the pressure transducers may be varied as desired and, for example, the transducer $T_A$ may be located adjacent the distal end of the catheter with transducers $T_B$ and $T_C$ spaced therefrom toward the proximal end. It is contemplated, for example, that these transducers may be used for simultaneously recording of pulmonary wedge pressure, right ventricular pressure, and atrial pressure. In such case, the transducers will be spaced approximately 10 centimeters apart.

As will be described in greater detail with respect to the three specific embodiments disclosed herein, filter F at the distal end of the catheter is chosen to transmit light above 800 nanometers, such as in the near infrared region, and to reflect light of shorter wavelengths.

The catheter 110 preferably takes the form of a torque controlled catheter, such as that constructed in accordance with the U.S. Patent to R. C. Stevens, U.S. Pat. No. 3,585,707, assigned to the same assignee as the present invention and the disclosure of which patent is herein incorporated by reference. Briefly, as described in that patent, the catheter is an intravascular catheter having an elongated body portion 115 and a tip portion 117 at the distal end of the catheter. The body portion 115 is reinforced so that it may be twisted at its proximal end to impart a twisting motion throughout its length. This body portion is constructed to have high longitudinal flexibility and high torsional control without being elastic. Moreover, the body portion includes tubing made up of an inner plastic tubular core covered by a braided wire intermediate sheath and an outer plastic covering which penetrates through the interstices in the braiding of the sheath and closely overlies the tubular core.

The tip portion 117 is designed to direct the catheter during insertion into a selected body vessel and is preferably formed with a tapered end as a pair of curves including a relatively sharp curve on the order of 45° just before the distal end thereof and a less sharp curve a short distance proximally thereof. The tip portion 117 does not employ a braided sheath and it is preferably more flexible than the body portion.

As will be described in greater detail hereinafter with respect to each embodiment of the invention, each of the transducers serves to measure pressure acting in a direction transversely of the optical axis of the optical fiber. For this purpose, each transducer is provided with an array of side ports spaced equidistant apart circumferentially about the catheter with each side port being covered with an elastic membrane which may, for example, take the form of silastic. Each membrane covers a transducer member constructed of flexible material having an index of refraction greater than the cladding and serves to make surface area contact with an uncladded core portion of the optical fiber. The contacting surface area will vary with pressure applied to the transducer acting transversely of the optical axis of the optical fiber. As the pressure increases, more light will be refracted and absorbed by the transducer member. Consequently, any light entering the proximal end of the optical fiber 112 will be modulated in each of the pressure transducers in dependence upon the magnitude of the pressures applied at the transducer sites. To assist in measuring pressure relative to atmospheric pressure, the catheter is vented, as with an aperture 114 in the wall of the catheter at a location near the proximal end where it is exterior to the patient.

In general, it is contemplated that for each embodiment herein, there will be provided a suitable light source 120 which transmits light into the proximal end of the optical fiber 112 so that the light may be modulated in dependence upon the pressure applied to each of the transducers $T_A$, $T_B$ and $T_C$. The input light may first pass through a beam splitter 122 which passes a portion of the light into the proximal end of the optical fiber 112 and directs the remaining light in an upward direction. Light that has been modulated and reflected from the distal end of the catheter is returned to the proximal end of the optical fiber 112 and is passed to the beam splitter 122 and a portion of this modulated light is then directed downwardly to an optical detector circuit 124. As will be described with respect to each embodiment, the detector circuitry operates to determine from the modulated light the values of the pressure $P_A$, $P_B$ and $P_C$ acting at the monitored sites A, B and C. This information may then be displayed as with the use of a conventional chart recorder 126 and/or displayed as with an oscilloscope 128. Having now provided a general description of one application of the invention, attention is directed to the specific description of each of the embodiments herein as presented below.

Figure 5:
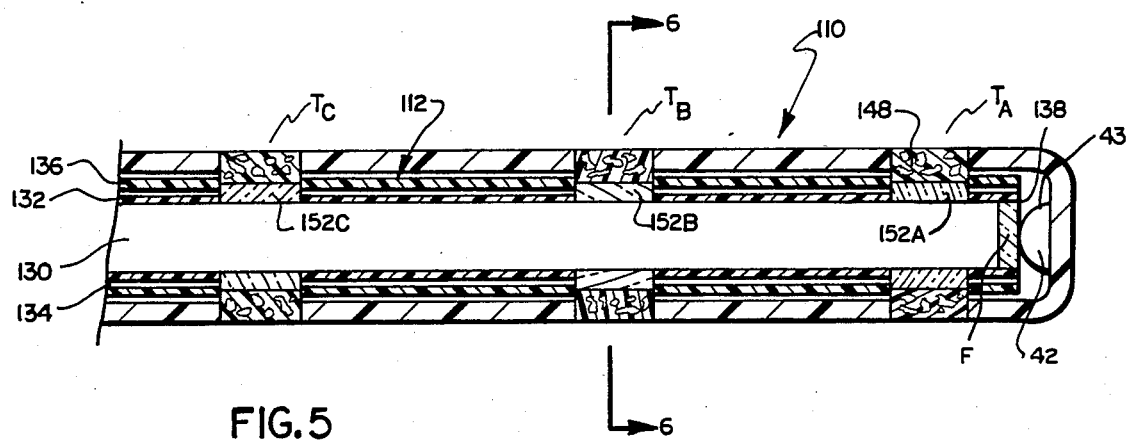
FIG. 5 is an enlarged sectional view of the distal end of the catheter illustrated in FIG. 4.

Reference is now made to FIG. 5 which presents an enlarged sectional view of the distal end of catheter 110 and showing pressure transducers $T_A$, $T_B$ and $T_C$. As seen, the catheter 110 is a single lumen, thin wall catheter, such as that provided by Cordis Corporation, and known as Cordis FR5 Thin Wall Catheter. This catheter may have a diameter on the order of 0.066 inches and is constructed of plastic material, such as polyurethane. The optical fiber 112 carried within the single lumen of the catheter preferably takes the form of a cladded multimode optical fiber. This fiber has a core 130 of a fluoropolymer of a diameter on the order of 400 micra. The core 130 is covered throughout essentially all of its length with cladding 132 constructed of an acrylic material having a thickness on the order of 16 micra. Surrounding the cladding 132 are Kevlar reinforcing strands 134 for purposes of strengthening the optical fiber 130. The Kevlar strands 134 are, in turn, covered with a layer of black Hytrel 136. Optical fibers, such as fiber 130, are commercially available. Light passing through the optical fiber 130 of wavelengths greater than 800 nanometers is passed by filter F suitably mounted, as by bonding, to an end hole 138 at the distal end of the catheter. Light of shorter wavelength is reflected by the filter.

Figure 6:
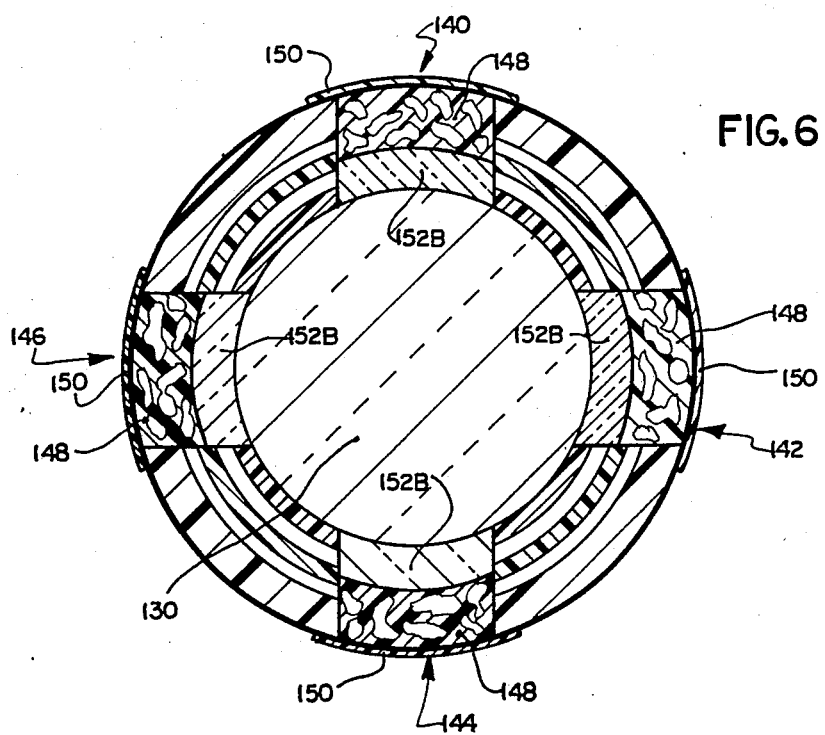
FIG. 6 is an enlarged sectional view taken along the line 6—6 looking in the direction of the arrows of FIG. 5.

At the locations for each of the pressure transducers $T_A$, $T_B$ and $T_C$, the cladding is removed. At each location there are provided four side ports 140, 142, 144, and 146 spaced in an annular array equidistant from each other, as is best shown in FIG. 6, which is a cross sectional view taken along line 6—6 looking in the direction of the arrows in FIG. 2. On each of the side ports, the cladding 132 and strands 134 and coating 136 are removed and replaced with a sponge-like transducer insert 148. The outer surface of each insert may, in turn, be coated with a protective membrane 150 which may be of a latex material and may be formed by applying viscous liquid of latex over the insert filled side port in adjacent exterior surface areas of the catheter and then air drying it. The membrane, while covering the insert, will adhere and form a seal with the outer surface of the catheter, but will not adhere to the sponge-like material forming the transducer inserts.

In the embodiment shown in FIGS. 5 and 6, the inner surface of each transducer insert faces a portion of the uncladded surface of the optical core 130. Intermediate the insert and the uncladded core 130, there is provided an optical coating defining a filter. These filters are illustrated and identified as filters 152A, 152B and 152C.

The filters 152A, 152B and 152C are standard coatings with each filter having a different functional relationship between index of refraction and wavelength. Thus, these filters are so chosen that each will partially refract a different waveband and reflect all other wavebands. This will be discussed in greater detail hereinafter.

In the construction of the embodiment as shown in FIG. 5, the cladding is removed at the locations for transducers $T_A$, $T_B$ and $T_C$. This may be accomplished in a controlled manner, as with the use of a solvent, such as tetrahydrofuran, so that the removal takes place only at desired locations. The transducer inserts 148 are constructed of a sponge-like material, such as polyurethane foam. This may take the form of hypol foamable hydrophilic polyurethane polymer which may be obtained from the Organic Chemicals Division of the W. R. Grace & Company. This is a porous material and includes interconnecting pores. The insert may be held in place by an interference fit.

At this point, it is to be noted that the index of refraction n is different for the various materials employed. Thus, the index of refraction n for the fiber core 130 is on the order of 1.5 and for the surrounding air within the air pockets and in the lumen, as vented to the atmosphere, is on the order of 1.0. The cladding 132 exhibits an index of refraction slightly less than that of core 130. However, for light to be transmitted through filters 152 and be absorbed or refracted by the sponge inserts 148, the filters 152 must have an index of refraction greater than that of cladding 132 and, in turn, the inserts 148 must have an index of refraction greater than that of the filters so as to refract light that is passed by the filters.

Each of the filters 152A, 152B and 152C pass light within a particular waveband and reflect the remaining light. Thus, for example, filter 152A reflects light within a waveband containing wavelengths $W_1$ and $W_2$ while passing light within a waveband containing light of wavelength $W_3$. This is illustrated in FIGS. 7A and 8A. Similarly, filter 152B passes light only within a waveband containing light in wavelength $W_2$, but reflects all remaining light, and this is illustrated in FIGS. 7B and 8B. Also, filter 152C passes light in a waveband containing wavelength $W_1$ while reflecting all remaining light, and this is illustrated in FIGS. 7C and 8C.

In this embodiment, the light source emits a broad band of light. A filament lamp or an arc lamp or other wide band light source may be employed as the light source 120. This light is passed by a beam splitter 122 and focused, as with a lens 174, into the proximal end of the optical fiber 112. The light that travels through the core 130 and which strikes the core-air interface (see FIG. 3) will be totally internally reflected. However, the light that strikes the core-sponge interface will be partially refracted and partially reflected. The amount of light that is refracted and thereby absorbed will be a function of the surface contact area. Thus, light that is traveling from the proximal end to the distal end of the catheter will pass through the transducer area and a portion of the light will be refracted in dependence upon the pressure P. The light that is internally reflected will be reflected back by the filter F or the mirror 42 at the distal end of the optical fiber. This reflected back light will also be attenuated as it passes the transducer area as it travels back toward the proximal end of the catheter. The intensity of light returning at the proximal end of the catheter will vary inversely with the pressure applied to the transducers.

At transducer $T_A$, only light that has been passed by filter 152A will be refracted and, hence, attenuated by the transducer insert 148. This light will be at wavelength $W_3$ and the remaining light is reflected by the filter 152A. Consequently, it is the light which exits from the proximal end of the optical fiber 112 at wavelength $W_3$ that includes the intelligence representing the pressure applied at transducer $T_A$.

In similar fashion, it is only the light exiting from the proximal end of the optical fiber at wavelength $W_2$ that includes the intelligence relative to the pressure applied at the transducer $T_B$. Also, it is only the light exiting from the proximal end of the optical fiber at wavelength $W_1$ that includes the intelligence as to the pressure at the transducer $T_C$.

Referring now to FIG. 8, it is seen that as the light exits from the proximal end of the optical fiber 112, it is applied by way of lens 174 to the beam splitter 122 and a portion is then directed in a downward direction. A first beam splitter 176 intercepts this light and directs a portion of it through a filter 178 that passes only light at wavelength $W_1$. This is detected by optical-electrical detector 180, which converts intelligence into an electric signal to drive a suitable meter 182 to provide an output indicative of the pressure at the transducer $T_C$. As the pressure at transducer $T_C$ increases, there will be a reduction in the amount of light returned to the proximal end at wavelength $W_1$. This is detected by detector 180 and displayed as with meter 182.

In a similar fashion, the light that is passed by the beam splitter 176 strikes a second beam splitter 184 and light reflected therefrom is passed through a filter 186 which passes light only at wavelength $W_2$. Detector 188 converts this information into an electrical signal which is supplied to a suitable meter 190. This circuitry provides an output indication representative of the pressure at transducer $T_B$. Also, light passing through the beam splitter 184 will strike an additional beam splitter 192 causing light reflected therefrom to be applied to a filter 194 which passes only light at wavelength $W_3$. This is detected by a suitable detector 196 which supplies an electrical signal to meter 198 for displaying an output signal representative of the pressure applied at transducer $T_A$.

The light from the light source 120 in FIG. 9 includes light in the red and infrared light regions, i.e., from at least 800 nanometers through 950 nanometers. This longer wavelength light of wavelength $W_4$ passes through the filter F at the distal end of the core 130 and is reflected by the elastic mirror 42 back into the core 130.

Referring now to FIG. 9, light exiting from the proximal end of the optical fiber 112 is reflected by splitter 22 and a portion of the light passes through beam splitters 176, 184 and 192. Light passing through beam splitter 192 strikes a mirror 185 and the reflected light is directed to a filter 187. This filter is selected to pass only light at wavelength $W_4$ and this is passed to a detector 183 which converts the optical intelligence into an electrical signal having a magnitude representative of the magnitude of reflected light at wavelength $W_4$. This electrical signal is representative of the total pressure $P_T$ applied to mirror 42 and includes static pressure $P_S$ and kinetic pressure $P_K$. The static pressure $P_S$ measured by transducer $T_A$ is represented by the output signal taken from detector 196. The outputs of detectors 196 and 189 are supplied to a subtractor 191 to provide an output representative of the kinetic pressure $P_K$. This may then be supplied to a suitable meter 193 which is calibrated to provide a velocity indication as a function of the square root of the kinetic pressure $P_K$. This, then, provides an indication of the velocity of blood flowing in the patient's blood vessel.

Reference is now made to another embodiment of the invention which is illustrated in FIGS. 10, 11, 12, 13 and 14. This embodiment is quite similar to that described thus far and, consequently, like components are identified with like character references and only the differences over the previous embodiment will be described in detail herein.

In this embodiment, no filters are employed. Instead, each of the transducer inserts 148A', 148B' and 148C' is doped with a different fluorescent dye. Each insert is covered on its exterior surface with a membrane, such as membranes 150 constructed in the same manner as that discussed hereinbefore with respect to membranes 150 in FIGS. 5 and 6. The fluorescent dye doped transducer inserts have been doped such that each fluoresces in a different waveband.

Figure 12C:
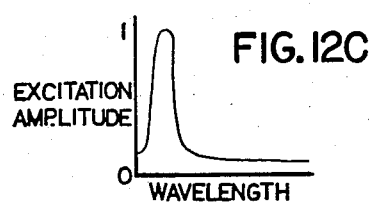
FIGS. 12A-12C are graphical waveforms illustrating excitation amplitude with respect to wavelength and are useful in describing the embodiment of FIGS. 10 and 11.
Figure 12B:
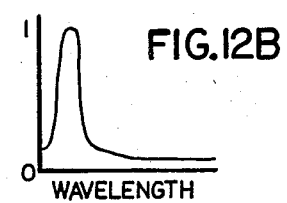
Figure 12A:
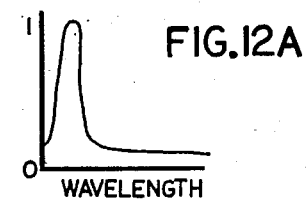
Figure 13C:
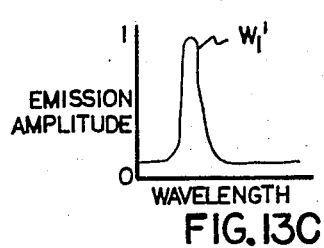
FIGS. 13A-13C are waveforms of emission amplitude versus wavelength and which are useful in describing the embodiment of FIGS. 10 and 11.
Figure 13B:
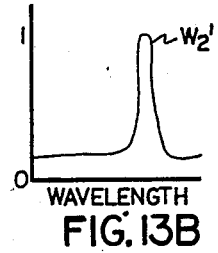
Figure 13A:
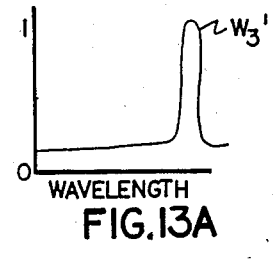
Figure 14:
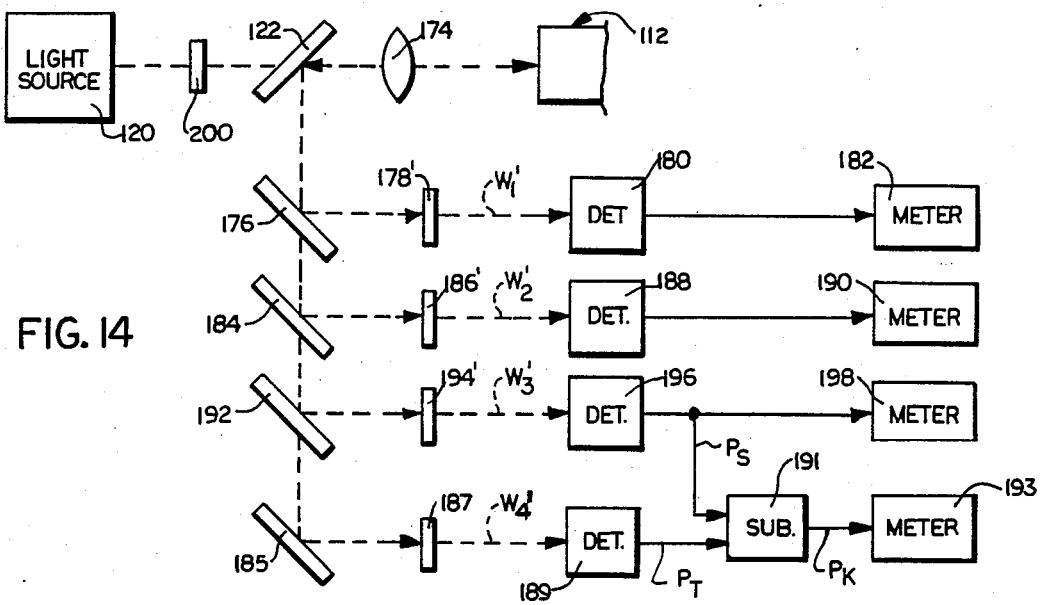
FIG. 14 is a schematic-block illustration of the detector circuitry employed in conjunction with the embodiment of FIGS. 10 and 11.
Figure 15:
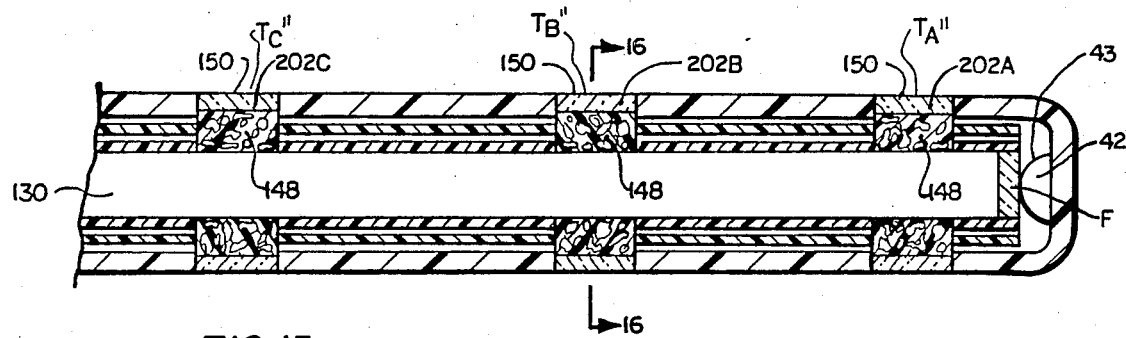
FIG. 15 is an enlarged sectional view of the distal end of the catheter showing another embodiment of the invention.
Figure 16:
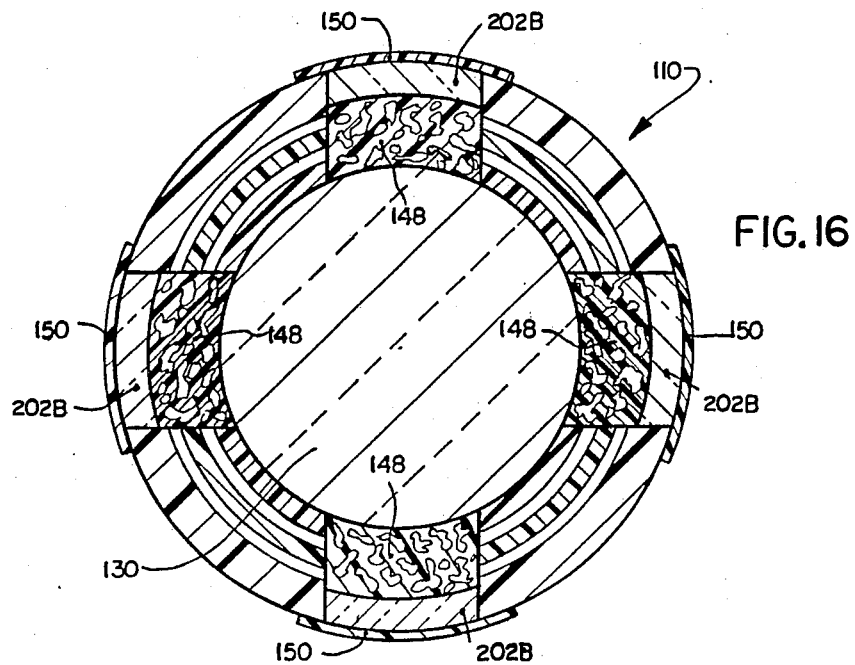
FIG. 16 is a cross sectional view taken along line 16—16 looking in the direction of the arrows in FIG. 15.

Reference is also made to FIGS. 12, 13 and 14. In this embodiment, light transmitted into the optical fiber 112 includes light at wavelengths capable of exciting the fluorescent doped inserts 148A', 148B' and 148C', but none of this excitation light is at any of the wavelengths at which these inserts fluoresce. For this reason, a filter 200 is employed for blocking light in the emission waveband of from approximately 350 to 700 nanometers. This filtered light is then passed by the beam splitter 122 and focused by lens 174 into the proximal end of the optical fiber 112. Within the catheter, the excitation light will be transmitted by core 130. This excitation light is at the excitation wavelengths from 300–350 nanometers and does not include light at a wavelength corresponding to that at which the fluorescent doped transducers fluoresce. In the example given, the excitation wavelengths may be considered a waveband which includes wavelengths from 300–350 nanometers, as is illustrated in FIGS. 12A, 12B and 12C. The transducer inserts will fluoresce at higher wavelengths with that of transducer insert 148C' having an emission wavelength of $W_1'$ on the order of 400 nanometers. The insert 148B' will have an emission wavelength $W_2'$ which will be on the order of 500 nanometers, and transducer 148A' will have an emission wavelength $W_3'$ on the order of 600 nanometers.

Thus, light passing through the optical fiber 110 within the core 130 will be refracted by the transducers 148A', 148B' and 148C' in accordance with the pressure exerted at each transducer. The greater the applied pressure, the greater will be the refraction of light. Consequently, the greater the pressure, then, the greater will be the amplitude or amount of energy emission at wavelengths $W_1'$, $W_2'$ and $W_3'$. Light exiting from the proximal end of the optical fiber 12 will contain light at each of these wavelengths $W_1'$, $W_2'$ and $W_3'$. This light is reflected in part by the beam splitter 122 (FIG. 14) and directed downwardly to the beam splitter 176. A portion of the light striking beam splitter 176 is reflected through a filter 178' which passes only light centered at the wavelength $W_1'$ indicative of the amount of pressure in transducer $T_C'$. This is detected by detector 180 and an electrical signal representative of the pressure level in tranducer $T_C'$ is then displayed as with meter 182. Similarly, a portion of the light passed through the beam splitter 176 to a beam splitter 184 which reflects a portion of the light to a filter 186' which passes only light centered about the wavelength $W_2'$. This is indicative of the amount of pressure at transducer $T_B'$ and this is converted into an electrical signal by detector 188 with the pressure reading then being displayed as with meter 190.

Also, a portion of the light is passed through a beam splitter 184 and is reflected by beam splitter 192 to a filter 194' which passes only light centered about wavelength $W_3'$. This is indicative of the amount of pressure at transducer $T_A'$ and this is converted into an electrical signal by detector 196 and the electrical output is supplied to meter 198 for providing a visual readout.

The light from the light source 120 in FIG. 14 includes light in the red and infrared light regions, i.e., from at least 800 nanometers through 950 nanometers. This longer wavelength light at wavelength $W_4'$ passes through the filter F at the distal end of the core 130 and is reflected by the elastic mirror 42 back into the core

130. The reflected light at wavelength $W_4'$ is representative of the total pressure $P_T$ acting on the mirror 42.

Referring now to FIG. 14, light exiting from the proximal end of the optical fiber 112 is reflected by splitter 122 and a portion of the light passes through beam splitter 176, 84 and 192. Light passing through beam splitter 192 strikes a mirror 185 and the reflected light is directed to a filter 187. This filter is selected to pass only light at wavelength $W_4'$ and this is passed to a detector 189 which converts the optical intelligence into an electrical signal having a magnitude representative of the magnitude of reflected light at wavelength $W_4'$. This electrical signal is representative of the total pressure $P_T$ and includes static pressure $P_S$ and kinetic pressure $P_K$. The static pressure $P_S$ measured by transducer $T_A$, is represented by the output signal taken from detector 196. The outputs of detectors 196 and 189 are supplied to a subtractor 191 to provide an output represenative of the kinetic pressure $P_K$. This may then be supplied to a suitable meter 193 which is calibrated to provide a velocity indication as a function of the square root of the kinetic pressure $P_K$. This, then, provides an indication of the velocity of blood flowing in the patient's blood vessel.

Reference is now made to FIGS. 15–18 which illustrate another embodiment of the invention. This embodiment is similar to that described hereinbefore and like components will be identified with like character references and only the differences between this embodiment and the previously described embodiments will be described below in detail.

Figure 10:
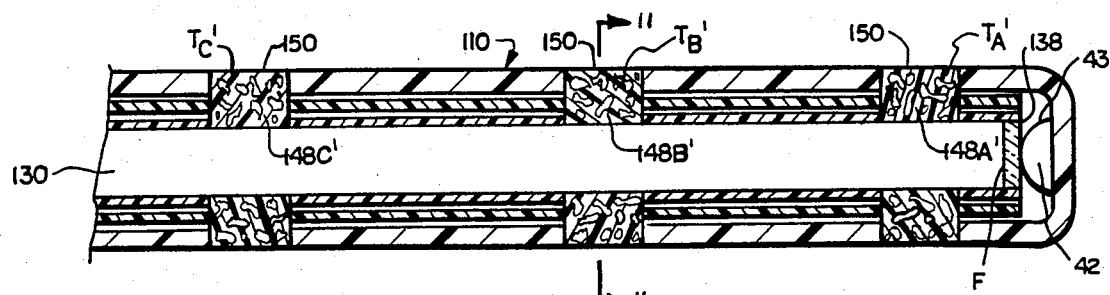
FIG. 10 is an enlarged sectional view of the distal end of the catheter showing another embodiment of the invention.
Figure 11:
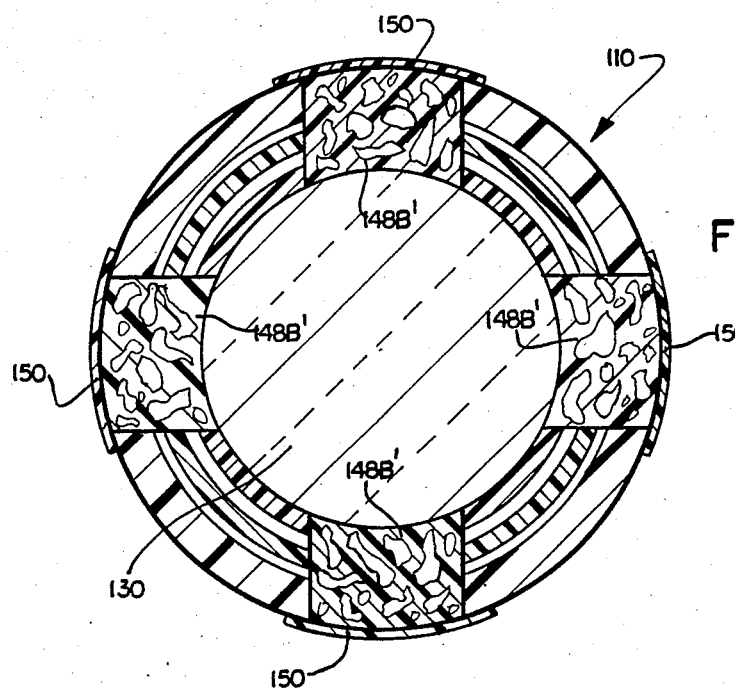
FIG. 11 is an enlarged cross sectional view taken along line 11—11 looking in the direction of the arrows in FIG. 10.

In this embodiment, as in the embodiment shown in FIGS. 10 and 11, the inserts 148 are mounted directly onto the uncladded surface areas of core 130. However, these inserts are not doped as in the case of inserts 148A', 148B' and 148C' of FIGS. 10 and 11. In this embodiment, a flexible, filter coating is applied to the exterior surface of each transducer insert. These filters are illustrated in the drawings as filters 202A, 202B and 202C applied respectively to the exterior surfaces of the transducer inserts 148. The filters, in turn, are each covered by means of a membrane 150, as in the other embodiments. The filters are sufficiently thin and flexible to transmit pressure to the inserts.

Figure 17C:
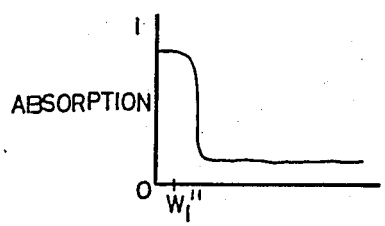
FIGS. 17A-17C are waveforms showing light absorption with respect to wavelength which is useful in describing the embodiment of FIGS. 15 and 16.
Figure 17B:
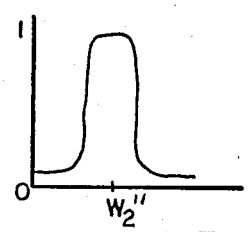
Figure 17A:
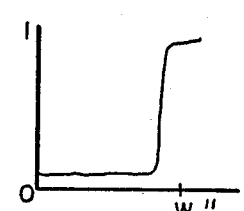

In this embodiment, the transducers are constructed from a nonabsorbent clear sponge-like material exhibiting an index of refraction greater than that of the cladding 132. Thus, the sponge-like material is transparent to light at all wavelengths. The surrounding filters, however, serve to absorb light of a particular wavelength and reflect all other wavelengths. For example, light passing through insert 148 at wavelength $W_1''$ will be refracted by filter 202C and absorbed. Light outside of this waveband will be reflected by the filter and/or by the surrounding membrane 150 and passed back through the insert into core 130. Similarly, at transducer $T_B''$, light which has been passed by the clear transducer insert 148 will be passed to the filter 202B which will, in turn, pass or absorb only light at wavelength $W_2''$ with the remaining light being reflected back into the core. Also, at transducer $T_A''$, light passing through the transducer insert 148 at wavelength $W_3''$ will be, in turn, passed by the filter 202A with the remaining light being reflected back into the core 130. This is indicated by the waveforms of FIGS. 17A–17C.

White light supplied by source 120 (FIG. 18) is passed by a beam splitter 122 and focused by a lens 174 into the proximal end of the optical fiber 112. The returning light includes information respecting the pressures at the three transducers in the sense of changes in the amount of light received at wavelengths $W_1''$, $W_2''$ and $W_3''$ from that which was originally introduced at those wavelengths into the optical fiber. For example, the returning light includes light at wavelength $W_1''$. Consequently, the returning light is reflected by beam splitters 122 and 176 and applied to a filter 178'' which passes only light at wavelength $W_1''$. This is detected by detector 180 and converted into an electrical signal which is supplied as one input into a ratio circuit 220.

Light which is reflected from the splitter 122 in an upward direction is supplied to a second beam splitter 222 which reflects a portion of that light through a filter 224. This filter serves to pass light only at wavelength $W_1''$ to a detector 226 which provides an electrical signal to a second input of the ratio circuit 220. The ratio circuit, then, compares the amplitude of light at wavelength $W_1''$ as it enters the optical fiber 112 with that which returns from the optical fiber to obtain a ratio signal. This ratio signal, identified as $V_1$, is then supplied to a suitable meter, such as meter 182, calibrated to provide an output pressure indication at transducer $T_A$ as a function of the ratio signal $V_1$. It is to be understood that FIG. 9 could be depicted similarly to improve the signal.

In a similar manner, the light returning from the optical fiber at wavelength $W_2''$ is detected and supplied to a second ratio circuit 230. In this case, the light which passes through splitter 222 is partially reflected from another splitter 232 and is supplied to a filter 234 which passes light only at wavelength $W_2''$, and this is detected by a detector 236. Detector 236 operates to provide an electrical signal to the second input of the ratio circuit 230 representative of the intensity of light at wavelength $W_2''$ as it originally entered the optical fiber 112. The ratio is determined by the ratio circuit 230 as output signal $V_2$ and this is supplied to meter 190 which is calibrated to provide an output indicative of the pressure at transducer $T_B''$ as a function of signal $V_2$.

Also, light returning from the optical fiber 112 at wavelength $W_3''$ is passed by the filter 194'' and detected by detector 196 and the electrical output signal therefrom is supplied to another ratio circuit 240. Light passing through the beam splitter 232 is reflected from a mirror 242 and passed to a filter 244 which passes only light at wavelength $W_3''$. This is detected by detector 246 which supplies an electrical output signal to a second input of the ratio circuit 240. The ratio circuit 240, in turn, provides a ratio output signal $V_3$ which is supplied to a meter 198 calibrated to provide a pressure reading as a function of ratio signal $V_3$.

Figure 18:
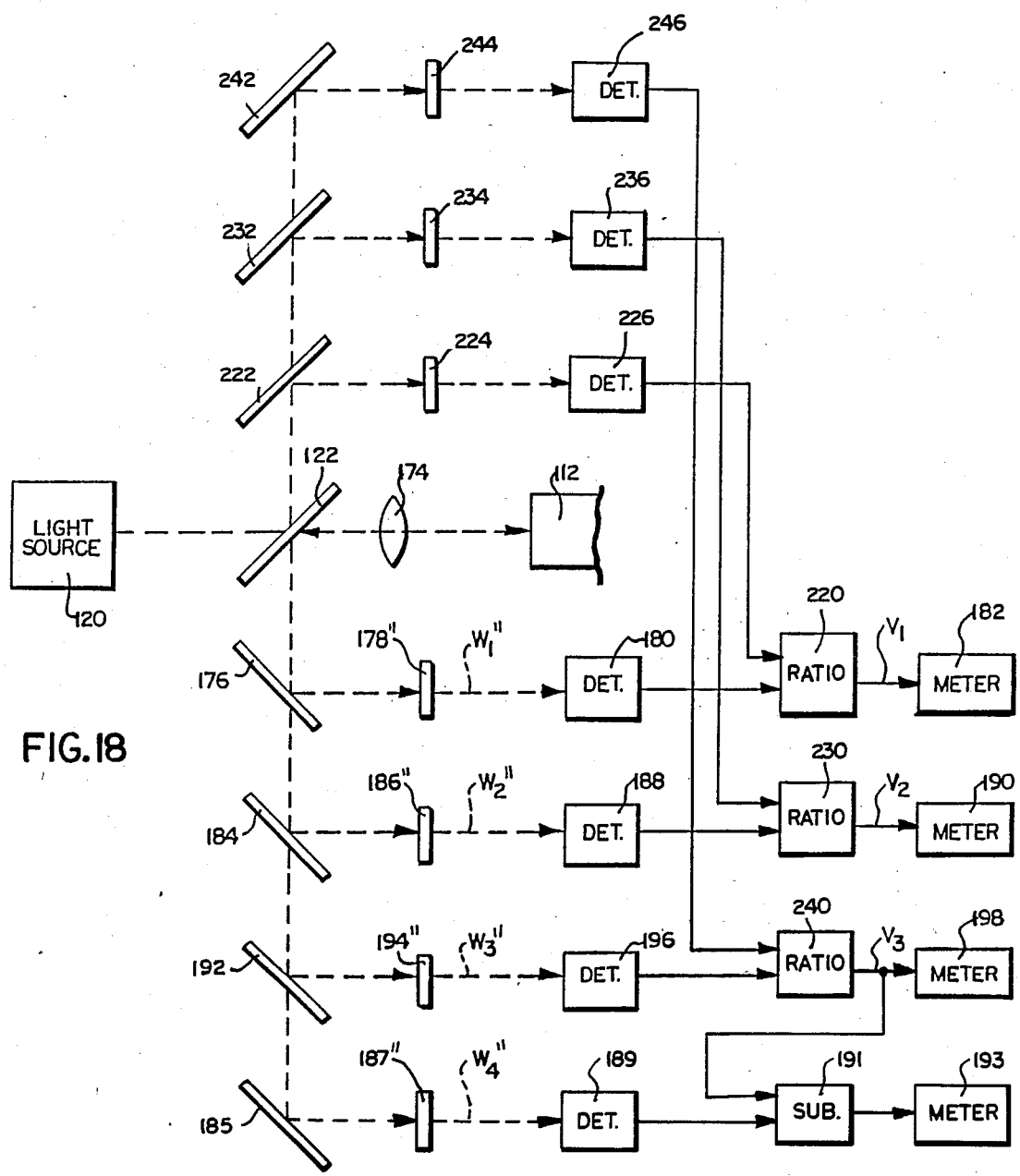
FIG. 18 is a schematic-block diagram illustration of the detector circuitry employed in conjunction with the embodiment of FIGS. 15 and 16.

The light from the light source 120 in FIG. 18 includes light in the red and infrared light regions, i.e., from at least 800 nanometers through 950 nanometers. This longer wavelength light at wavelength $W_4''$ passes through the filter F at the distal end of the core 130 and is reflected by the elastic mirror 42 back into core 130. The reflected light at wavelength $W_4''$ is representative of the total pressure $P_T$ acting on the mirror 42.

Referring now to FIG. 18, light exiting from the proximal end of the optical fiber 112 is reflected by splitter 122 and a portion of the light passes through beam splitters 176, 184 and 192. Light passing through beam splitter 192 strikes a mirror 185 and the reflected light is directed to a filter 187''. This filter is selected to pass only light at wavelength $W_4''$ and this is passed to a detector 189 which converts the optical intelligence into an electrical signal having a magnitude representative of the magnitude of light at wavelength $W_4''$. This electrical signal is representative of the total pressure $P_T$ and includes static pressure $P_S$ and kinetic pressure $P_K$. The static pressure $P_S$ measured by transducer $T_A''$ is represented by the output signal $V_3$ taken from circuit 240. The outputs of circuits 189 and 240 are supplied to a subtractor 191 to provide an output representative of the kinetic pressure $P_K$. This is then supplied to a suitable meter 193 which is calibrated to provide a velocity indication as a function of the square root of the kinetic pressure $P_K$. This, then, provides an indication of the velocity of blood flowing in the patient's blood vessel.

Although the invention has been described in conjunction with preferred embodiments, it is to be appreciated that various modifications may be made without departing from the spirit and scope of the invention as defined by the appended claims.

Having described specific preferred emboidments of the invention, the following is claimed:

1. Apparatus for use in a device for measuring the velocity of blood flowing in a blood vessel in a body, comprising:
    an elongated tubular catheter having a proximal end and a distal end with the latter adapted to be inserted into a blood vessel such that said blood flows parallel to said catheter;
    an elongated optical fiber member carried within said catheter and having a proximal end and a distal end and extending throughout essentially the length of said catheter;
    first pressure transducer means carried by said catheter adjacent the distal end thereof and responsive to static pressure acting transversely of said catheter for modulating the intensity of any light passing through said optical fiber inversely proportional to the magnitude of said transversely acting static pressure; and
    second pressure transducer means carried by said catheter at the distal end thereof and responsive to total pressure, including static pressure and kinetic pressure, acting parallel to said catheter, for modulating the intensity of any light passing through said optical fiber proportional to the magnitude of said total pressure, whereby the velocity of blood in said vessel can be determined as a function of the difference between said total pressure and said transversely acting static pressure.

2. Apparatus as set forth in claim 1 including means for providing an output indication of said velocity of blood as a function of the difference between said total pressure and said transversely acting static pressure.

3. Apparatus as set forth in claim 1 wherein said first transducer means and said second transducer means are respectively constructed in such a manner that each acts to vary the intensity of light passing through said optical fiber in respectively opposing manners so that any variation in the intensity of light returning to the proximal end is due mainly to variations in kinetic pressure and, hence, to velocity of blood.

4. Apparatus as set forth in claim 1 wherein said second pressure transducer means includes elastic mirror means located forwardly of the distal end of said optical fiber member for reflecting any light received from said optical fiber member back into said optical fiber member proportional to said total pressure so that the reflected light directed to the proximal end thereof is indicative of said total pressure.

5. Apparatus as set forth in claim 4 wherein said elastic mirror means has a light reflective convex surface facing the distal end of said optical fiber member and serves to make variable surface area contact therewith in dependence upon the magnitude of said total pressure so that the amount of light returned toward the proximal end of said optical fiber member varies with said total pressure.

6. Apparatus as set forth in claim 5 wherein said elongated optical fiber member has a light transmitting core coaxially surrounded by cladding means essentially throughout its length with said core being uncladded for at least a portion of its length proximal to the distal end thereof and said first pressure transducer means includes a flexible transducer member having a pitted surface facing said uncladded core portion making surface area contact therewith such that the contacting surface area varies with pressure applied to said transducer member acting transversely thereof, said transducer member being constructed of material exhibiting a greater index of refraction than that of said cladding means so that the intensity of any light passing through said core proximate to said transducer means is modulated inversely in its intensity as a function of said pressure.

7. Apparatus as set forth in claim 6 further including means for supplying light into the proximal end of said optical fiber member and detecting means for receiving light exiting from the proximal end, said detecting means including means for providing an output indication of blood velocity as a function of the difference between said total pressure and said transversely acting static pressure.

8. Apparatus as set forth in claim 7 wherein said detecting means includes means for providing a first output indication representative of said total pressure and second means for providing an output indication representative of said transversely acting static pressure and third means for providing an output indication of blood velocity as a function of the difference between said total pressure and said transversely acting static pressure.

9. Apparatus as set forth in claim 8 wherein said third means includes means providing said blood velocity indication dependent on the squareroot of the difference between said total pressure and said transversely acting static pressure.

10. Apparatus as set forth in claim 7 including filter means interposed between the distal end of said optical fiber member and said elastic mirror means for passing light beyond wavelength W and reflecting light at shorter wavelengths back into the proximal end of said optical fiber means so that the light reflected back into the proximal end of said optical fiber means from said elastic mirror is of a wavelength greater than wavelength W.

11. Apparatus as set forth in claim 4 including a plurality of said first pressure transducer means carried by said catheter at spaced apart locations along its length adjacent the distal end thereof for simultaneously measuring static blood pressure acting transversely of said catheter at different sites within said blood vessel whereby said apparatus serves to simultaneously measure static blood pressure at multiple sites while also measuring the velocity of blood within said blood vessel.

12. Apparatus as set forth in claim 11 wherein each of said plurality of said first pressure transducer means includes light wavelength dependent means for modulating light at a particular wavelength different from that at said other transducer means.

13. Apparatus as set forth in claim 12 wherein each said first transducer means includes a transducer filter means for passing light within one wavelength range less than wavelength W while reflecting light of other wavelengths.

14. Apparatus as set forth in claim 13 wherein said second pressure transducer means includes light filter means interposed between the distal end of said optical fiber member and said elastic mirror means for passing light greater than wavelength W while reflecting light of shorter wavelengths so that variations in said total pressure will cause light greater than wavelength W to be varied in its intensity in proportion to the magnitude of said total pressure.

* * * * *